United States Patent
Guo

(10) Patent No.: US 9,624,252 B2
(45) Date of Patent: Apr. 18, 2017

(54) SELECTIVE NUCLEIC ACID FRAGMENT RECOVERY

(71) Applicant: Omega Bio-Tek, Inc., Norcross, GA (US)

(72) Inventor: Qi Guo, Norcross, GA (US)

(73) Assignee: Omega Bio-tek, Inc., Norcross, GA (US)

( * ) Notice: Subject to any disclaimer, the term of this patent is extended or adjusted under 35 U.S.C. 154(b) by 74 days.

(21) Appl. No.: 14/556,493

(22) Filed: Dec. 1, 2014

(65) Prior Publication Data

US 2015/0166592 A1    Jun. 18, 2015

Related U.S. Application Data

(63) Continuation of application No. PCT/US2013/043849, filed on Jun. 3, 2013.

(60) Provisional application No. 61/689,221, filed on Jun. 1, 2012.

(51) Int. Cl.

| | |
|---|---|
| *C12Q 1/68* | (2006.01) |
| *C12M 1/00* | (2006.01) |
| *C12P 19/34* | (2006.01) |
| *C07H 21/02* | (2006.01) |
| *C07H 1/06* | (2006.01) |
| *C40B 40/06* | (2006.01) |
| *G01N 31/22* | (2006.01) |
| *C12N 15/10* | (2006.01) |
| *C07H 21/04* | (2006.01) |

(52) U.S. Cl.
CPC ............. *C07H 1/06* (2013.01); *C07H 21/04* (2013.01); *C12N 15/1006* (2013.01)

(58) Field of Classification Search
CPC ........ C12Q 1/68; C12M 1/34; C12N 15/1006; G01N 33/553

USPC ............ 435/6.1, 91.1, 91.2, 283.1; 536/23.1, 536/127; 506/16; 422/430

See application file for complete search history.

(56) References Cited

U.S. PATENT DOCUMENTS

| | | | |
|---|---|---|---|
| 5,234,809 A | 8/1993 | Boom et al. | |
| 8,048,681 B2 * | 11/2011 | Yamashita | C07H 21/00 210/294 |
| 8,202,427 B2 * | 6/2012 | Sauer | B03C 1/01 210/638 |
| 2007/0190535 A1 * | 8/2007 | Hall | C12N 15/101 435/6.12 |
| 2010/0056769 A1 | 3/2010 | Ritt et al. | |

FOREIGN PATENT DOCUMENTS

| | | |
|---|---|---|
| EP | 1 529 840 A1 | 5/2005 |
| WO | 2007/140417 A2 | 12/2007 |
| WO | 2010//015835 A1 | 2/2010 |

OTHER PUBLICATIONS

PCT International Search Report and Written Opinion for PCT Application No. PCT/US2013/043849 mailed Sep. 11, 2013 (12 pages).

* cited by examiner

*Primary Examiner* — Narayan Bhat
(74) *Attorney, Agent, or Firm* — Jin & Fang, LLP; Lei Fang, Esq.

(57) ABSTRACT

The invention provides methods and kits for nucleic acid purification and fragment selection and recovery. By adjusting salt concentrations and/or pH of the binding buffers, only nucleic acid fragments with desired size ranges are able to reversibly and non-specifically bind to a solid surface in certain salt concentrations and/or pH conditions, and can be subsequently eluted and/or recovered from the solid surface in water and/or a low salt eluting buffer.

11 Claims, 14 Drawing Sheets

SELECTIVE NUCLEIC ACID FRAGMENT RECOVERY

CROSS REFERENCES TO RELATED APPLICATIONS

This application is a continuation of PCT Application No. PCT/US2013/043849 filed on Jun. 3, 2013 which claims priority from U.S. Provisional Application Ser. No. 61/689,221 filed on Jun. 1, 2012, which are incorporated herein by reference in their entirety.

FIELD OF THE INVENTION

The invention relates to methods for nucleic acid purification and fragment size selection and recovery.

BACKGROUND OF THE INVENTION

Many molecular biology applications, such as capillary electrophoresis, nucleotide sequencing, require the isolation of high quality nucleic acid preparations. Quality is a particularly important factor for capillary electrophoresis for all sequencing methods and for gene therapy protocols. Quantity is also an equally important consideration for some applications, for example, large scale genomic mapping and sequencing projects, which require the generation of hundreds of thousands of high quality DNA templates.

The emergence of new technologies such as Next Generation Sequencing (NGS) requires high quality DNA sample preparation with precise size control of certain groups of DNA fragments. After DNA fragmentation or shearing, the library construction process for next generation sequencing mostly requires fragments selection regardless of the platform. Obtaining high recovery post fragment selection is becoming an important contributor for the reduction of sequencing bias. For example, to prepare a DNA library for Illumina NGS platform, recovery of DNA fragments in the 150-500 bp range is critical for better sequencing results. Other NGS platforms require DNA fragments ranging between 300-700 bp.

There are two common methods to perform size selection for NGS library preparation. One method is to run the fragmented DNA into agarose gel and then cut the gel with selected DNA size and then recover the DNA fragments from gel. This method is accurate, but it is very slow and labor intensive.

Another common used method to prepare size selection of fragmented DNA is to bind DNA on magnetic beads coated with functional groups such as a carboxyl group by adjusting the concentration of polyethylene glycol (PEG) and salts. See U.S. Pat. No. 6,534,262. This method fragments DNA efficiently and can be easily adapted in an automated platform to process large number of samples at one time. However, this method does not work well for DNA fragmentation when the DNA fragments are larger than 400 bp. The unwanted large DNA fragments decrease the data quality for the subsequent NGS results and waste the capacity of the instrument. For an NGS platform that requires large DNA fragments, for instance the NGS platform for Roche 454 Genome Sequencer, this method is not suitable.

U.S. Pat. No. 5,234,809 describes a method that uses solid phase particles to specifically and/or non-specifically bind nucleic acids from a sample in the presence of chaotropic salts, such as guanidinium salt, sodium iodide, and potassium iodide. However, this method does not provide any size control on nucleic acids fragments.

Therefore, the growing application of next generation sequencing (NGS) demands new nucleic acid purification and fragment size selection methods that provide high nucleic acid recovery and precise fragment size control.

SUMMARY OF THE INVENTION

The invention provides methods and kits for nucleic acid purification and fragment size selection. In certain embodiments, the invention provides a method to selectively recover nucleic acid fragments comprising: a) mixing target nucleic acids with a binding buffer having a selected pH, and salt concentration to allow the nucleic acid fragments with a desired size range to be bound to a solid surface; b) applying the mixture from step a) to the solid surface so that only the nucleic acid fragments with the desired size range reversibly and non-specifically bind to the solid surface; and c) selectively recovering the bound nucleic acid fragments with the desired size range by eluting the bound nucleic acid fragments from the solid surface with an eluting buffer.

In certain embodiments, the binding buffer used in the invention method comprises a chaotropic salt. Examples of chaotropic salts include, but not limited to, guanidium hydrochloride (GHCl), guanidium thiocyanate (GITC), sodium iodide (NaI), and sodium perchlorate and mixtures thereof. In certain embodiments, the concentration of chaotropic salt of the binding buffer is adjusted so that only certain nucleic acid fragments with a desired size range are able to reversibly and non-specifically bind to the solid surface, and are subsequently eluted from the solid surface with an eluting buffer. In certain embodiments, the concentration of guanidium hydrochloride (GHCl) or guanidium thiocyanate (GITC) is between 0.8-5.0M; the concentration of sodium iodide (NaI) is between 0.8-7.0M; and the concentration of sodium perchlorate is between 1.0-7.0M. In certain embodiments, the chaotropic salt concentration in the binding buffer is adjusted by diluting the binding buffer with water.

The invention provides that by adjusting the chaotropic salt concentration in the binding buffer, only certain nucleic acid fragments with a desired size range are able to bind to a solid surface, the undesired nucleic acid fragments remained in the sample mixture with the binding buffer, and are discarded after centrifugation. In certain embodiments, the solid surface includes, but is not limited to, silica membrane filter column or silica coated magnetic microparticles (beads). In certain embodiments, the nucleic acid fragments include, but are not limited to, DNA fragments, RNA fragments, or PNA fragments.

In certain embodiments, the invention provides a method to selectively recover DNA fragments from a silica membrane filter column with the desired size range less or equal to 100 bp, less or equal to 200 bp, or less or equal to 300 bp. The inventive method comprises mixing the target DNA samples (e.g., 100 μl) with a binding buffer (e.g., 100 μl) comprising 4M guanidium thiocyanate (GITC, pH 7.0), wherein each DNA sample mixture (200 μl in total) is further diluted with 200 μl, 300 μl, or 400 μl water, before each mixture is separately applied into a silica membrane column. Only DNA fragments less or equal to 100 bp when diluted with 200 μl water with the final concentration of GITC of about 1.0M, DNA fragments less or equal to 200 bp when diluted with 300 μl water with the final concentration of GITC of about 0.8M, and DNA fragments less or equal to 300 bp when diluted with 400 μl water with the final concentration of GITC of about 0.7M, are able to bind to the silica membrane column, and are subsequently eluted from the silica membrane column and recovered in water and/or an eluting buffer containing low salt. The pH of each mixture is about 7.0 and may vary slight due to the binding buffer mixed with the DNA sample.

In other embodiments, the invention provides a method to selectively recover DNA fragments from silica coated microparticles with the desired size range less or equal to 200 bp, less or equal to 300 bp, or less or equal to 400 bp. The inventive method comprises mixing the target DNA samples with a binding buffer comprising 4M guanidium thiocyanate (GITC), wherein each DNA sample mixture is further diluted with 200 µl, 300 µl or 400 µl water, before each mixture is further combined with silica coated microparticles. Only DNA fragments less or equal to 200 bp when diluted with 200 µl water with the final concentration of GITC of about 1.0M, DNA fragments less or equal to 300 bp when diluted with 300 µl water with the final concentration of GITC of about 0.8M, and DNA fragments less or equal to 400 bp when diluted with 400 µl water with the final concentration of GITC of about 0.7M, are able to bind to the silica coated microparticles, and are subsequently eluted from the microparticles and recovered in water and/or an eluting buffer containing low salt. Similarly, the pH of each mixture is about 7.0 and may vary slight due to the binding buffer mixed with the DNA sample.

The invention further provides a method to selectively recover nucleic acid fragments with desired size ranges by adjusting either the salt concentration, or pH, or both, of the binding buffers used in the process. In certain embodiments, the invention provides a method to selectively recover nucleic acid fragments with a desired size range, for instance, 150 bp-700 bp DNA fragments. The inventive method comprises the steps of: a) providing a first sample mixture by mixing target nucleic acids with a first binding buffer, wherein a salt concentration or pH of said first binding buffer is adjusted to allow only larger nucleic acid fragments, e.g., more than 700 bp DNA fragments, to bind to a solid surface; b) applying said first sample mixture from step a) to the first solid surface; c) collecting a flow-through solution from centrifuging the first solid surface with the first sample mixture; d) providing a second sample mixture by mixing the flow-through solution with a second binding buffer, wherein a salt concentration or pH of said second binding buffer is adjusted to allow only nucleic acid fragments with a smaller desired size range, e.g., 150 bp-700 bp DNA fragments, to bind to a solid surface; e) applying the second sample mixture from step d) to a second solid surface; and e) selectively eluting and recovering the nucleic acid fragments with the desired smaller size range, e.g., 150 bp-700 bp DNA fragments, by eluting the bound nucleic acid fragments from said second solid surface and recovered them in water and/or an eluting buffer comprising a low salt.

The invention provides that the DNA binding ability varies upon a combination of the concentration of a chaotropic salt and the pH in a binding buffer. In certain embodiments, when the binding buffer contains GITC at a final concentration of about 1.0M, at pH about 5.33, majority of DNA fragments having 500 bp or greater are able to bind to a solid surface; at pH about 4.92, majority of DNA fragments having 400 bp or greater are able to bind to a solid surface; at pH about 3.44, majority of the DNA fragments having 300 bp or greater are able to bind to a solid surface; at pH about 2.57, majority of the DNA fragments having 250 bp or greater are able to bind to a solid surface (See the illustration Table below).

In other embodiments, when the binding buffer contains GITC at a final concentration of about 2.5M, at pH about 5.67, majority of DNA fragments having 100 bp or greater are able to bind to a solid surface; at pH about 5.75, majority of DNA fragments having 110 bp or greater are able to bind to a solid surface; at pH about 5.83, majority of the DNA fragments having 120 bp or greater are able to bind to a solid surface; at pH about 5.90, majority of the DNA fragments having 130 bp or greater are able to bind to a solid surface; at pH about 5.96, majority of the DNA fragments having 140 bp or greater are able to bind to a solid surface; and at pH about 6.02, majority of the DNA fragments having 150 bp or greater are able to bind to a solid surface (See the illustration Table below).

| 1.0M GITC/pH | DNA Binding | 2.5M GITC/pH | DNA Binding |
| --- | --- | --- | --- |
| 5.33 | >500 bp | 5.67 | >100 bp |
| 4.92 | >400 bp | 5.75 | >110 bp |
| 3.44 | >300 bp | 5.83 | >120 bp |
| 2.57 | >250 bp | 5.90 | >130 bp |
|  |  | 5.96 | >140 bp |
|  |  | 6.02 | >150 bp |

In certain embodiments, the first and/or second binding buffer comprises a chaotropic salt including, but not limited to, guanidium hydrochloride (GHCl) in a concentration between 0.8-5.0M, guanidium thiocyanate (GITC) in a concentration between 0.8-5.0M, sodium iodide (NaI) in a concentration between 0.8-7.0M, and sodium perchlorate in a concentration between 1.0-7.0M. In some embodiments, the first binding buffer comprises a low chaotropic salt concentration, for instance, 0.85M guanidine thiocyanate (pH 7.0), whereas the second binding buffer comprises a high chaotropic salt, for instance, 4.0M guanidine thiocyanate (pH 6.5). By adjusting the salt concentrations in the first and second binding buffers, certain nucleic acid fragments are selectively bound to the first or second solid surface, respective, and can be subsequently eluted and recovered from either solid surface in water and/or an eluting buffer.

In other embodiments, pH of the first and/or second binding buffer is also adjusted. The invention provides that binding ability of nucleic acid fragments is sensitive to pH of the binding buffer. Lower pH facilitates larger nucleic acid fragments' binding ability to a solid surface, whereas smaller nucleic acid fragments lose binding ability to the solid surface when pH increases (See the illustration Table above). In certain embodiments, the pH of a binding buffer is adjusted using an acid or acidic salt, such as Tris-HCl, sodium phosphate, or other phosphate salt, to allow larger nucleic acid fragments to be bound to the solid surface. In other embodiments, the pH of a binding buffer is adjusted using a base or basic salt, such as NaOH, to remove smaller nucleic acid fragments and allow only certain nucleic acid fragments with desired size ranges to be bound to the solid surface, and subsequently recovered therefrom. In certain embodiments, the pH of the binding buffer ranges from about 5.5 to about 7.5.

The invention further provides kits for selectively recovering nucleic acid fragments with desired size ranges. The inventive kits comprise: a) one or more binding buffers for selective binding of nucleic acid fragments to a solid phase; b) one or more solid phase coated with some functional group on the surface; c) other reagents for nucleic acid purification and recovery; and d) instructions providing guidelines and protocols for selectively recovering nucleic acid fragments with desired size ranges. In certain embodiments, the solid phase is silica membrane filter column or silica coated magnetic microparticles. In certain embodiments, the reagents for nucleic acid purification and recovery include, but are not limited to, wash buffer, eluting buffer, and/or water.

DETAILED DESCRIPTION

Figure 1:
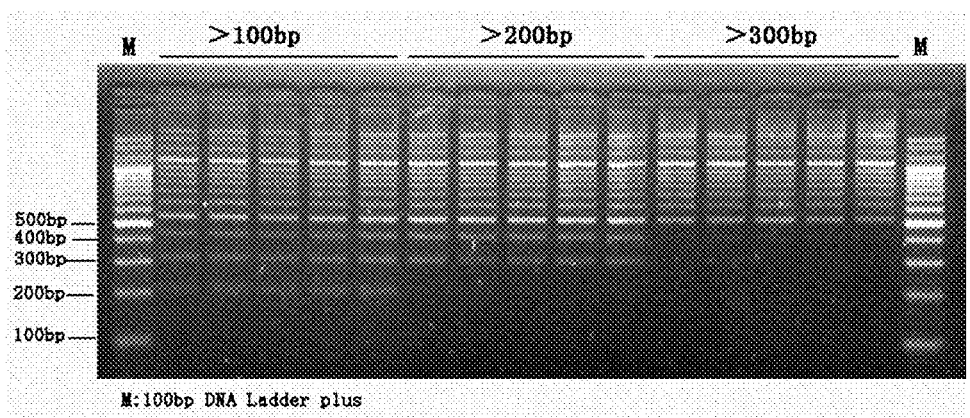
FIG. 1 shows the results on EtBr-stained agarose gel electrophoresis illustrating the separation and selection of DNA fragments eluted and recovered from a silica column using a DNA size selection binding buffer diluted with different amount of water.

The invention provides a quick, simple, and high throughput method of nucleic acid purification and fragment selection and recovery. By adjusting salt concentrations and/or pH of the binding buffers, the invention provides a method in which only nucleic acid fragments with desired size ranges are able to reversibly and non-specifically bind to a solid surface in certain salt concentrations and/or pH conditions, and can be subsequently eluted and recovered from the solid surface by water or a low salt eluting buffer. The nucleic acid fragments with desired size ranges obtained by the inventive method can be used in later nucleic acid based biochemical and diagnostic detection procedures, such as large scale genomic mapping, post DNA shearing, library construction, and for next generation sequencing platform. The invention further provides kits for purifying and selecting nucleic acid fragments with desired size ranges.

As used herein, "nucleic acid" refers to any polynucleotide including, but not limited to, DNA, RNA, or polyamide nucleic acids (PNA), naturally occurring or synthetic modifications thereof, and/or any combinations thereof. In certain embodiments, the nucleic acid fragments refer to DNA fragments, which can be single, double or triple stranded, and in any form such as, linear or circular. In other embodiments, the nucleic acid fragments refer to RNA or PNA fragments. Nucleic acids can be separated and isolated from any other biomolecules, including but not limited to, proteins, monosaccharides, polysaccharides, lipids, RNAs, and any other cellular components. Although the inventive method as described herewith references DNA fragments as an example, it is to be understood that the invention method can also be used to selectively recover RNA or PNA or any nucleic acid fragments with desired size ranges in a similar manner, as manipulating salt concentrations and/or pH conditions of binding buffer(s) can control binding abilities of nucleic acids to a solid phase selectively based on a size difference. The invention provides that because small nucleic acid fragments require higher salt concentration and/or lower pH for strong binding to a silica membrane filter column or silica coated magnetic microparticles/beads, salt concentrations and/or pH can be selectively manipulated to release nucleic acid fragments bound to silica material on the basis of size.

As used herein, nucleic acids can be obtained from any sample materials containing nucleic acids. For example, the sample materials can be any materials from foods and allied products, clinical and environmental samples. In certain embodiments, the sample material is a biological sample. In certain embodiments, such biological material comprises all types of mammalian and non-mammalian animal cells, plant cells and bacteria. Representative samples include whole blood and blood-derived products, such as plasma or buffy coat, saliva, semen, tissue homogenates, urine, faeces, cerebrospinal fluid or any other body fluids, tissues, cell cultures, cell suspensions etc. Biological material also includes environmental samples such as soil, water, or food samples. The sample material may also include relatively pure or partially purified starting materials, such as semi-pure preparations obtained by other cell separation processes, such as plasmids, PCR products, genotyping and/or sequencing starting products.

The invention provides methods to selectively recover nucleic acid fragments comprising: a) mixing target nucleic acids with a binding buffer having a selected pH and salt concentration to allow the nucleic acid fragments with a desired size range to be bound to a solid surface; b) applying the mixture from step a) to the solid surface so that the nucleic acid fragments with the desired size range reversibly and non-specifically bind to the solid surface; and c) selectively recovering the bound nucleic acid fragments with the desired size range by eluting the bound nucleic acid fragments from the solid surface with an eluting buffer.

As used herein, the "binding buffer" refers to any buffer solution that is now known or later developed to be used in nucleic acid isolation and purification process. The binding buffer used in the instant invention comprises any salt commonly used for nucleic acid binding and precipitation. In certain embodiments, the binding buffer used in the invention method comprises a chaotropic salt. Examples of chaotropic salts include, but not limited to, guanidium hydrochloride (GHCl), guanidium thiocyanate (GITC), sodium iodide (NaI), sodium perchlorate, and mixtures thereof. In certain embodiments, the concentration of chaotropic salt of the binding buffer is adjusted so that only certain nucleic acid fragments with desired size range are able to reversibly and non-specifically bind to the solid surface, and are subsequently eluted from the solid surface with an eluting buffer. In certain embodiments, the concentration of guanidium hydrochloride (GHCl) or guanidium thiocyanate (GITC) is between 0.8-5.0M; the concentration of sodium iodide (NaI) is between 0.8-7.0M; and the concentration of sodium perchlorate is between 1.0-7.0M. The invention does not limit the scope of different types of salt present in the binding buffer. In certain embodiments, the binding buffer comprises guanidine thiocyanate (4M), Tris-HCl (100 mM, pH 7.0), and EDTA (10 mM). In other embodiments, the first binding buffer comprises guanidine thiocyanate (0.85M), Tris-HCl (100 mM, pH 7.0) and EDTA (10 mM), and the second binding buffer comprises guanidine thiocyanate (4M) and Tris-HCl (100 mM, pH 6.5). In yet other embodiments, the first binding buffer comprises guanidine thiocyanate (1.3M), sodium dihydrogen phosphate (0.3M, pH 6.0), and the second binding buffer comprises guanidine thiocyanate (4M) and Tris-HCl (100 mM, pH 6.5).

In certain embodiments, the chaotropic salt concentration in the binding buffer is adjusted by diluting the binding buffer with certain amount of water or any other solutions and/or solvents that are capable of adjusting the salt concentration of the binding buffer. Methods for adjusting a salt concentration in a binding buffer are well known in the art, and the invention does not limit the scope of different methods for adjusting a salt concentration of a binding buffer.

The invention provides that by adjusting the chaotropic salt concentration in the binding buffer, only certain nucleic acid fragments with a desired size range are able to bind to a solid surface, whereas the undesired nucleic acid fragments remained in the sample mixture with the binding buffer, and are discarded after centrifugation. As used herein, the solid surface refers to a surface of any solid support including any of the well-known supports or matrices which are currently widely used or proposed for immobilization or separation. These may take the form of beads, particles, sheets, gels, filters, membranes, fibres, capillaries, or microtitre strips, tubes, plates or wells. The support may be made of glass, silica, latex or a polymeric material. Preferred are materials presenting a high surface area for binding of nucleic acids. Such supports will generally have an irregular surface and may be for example porous or particulate, e.g. particles, fibres, webs, sinters or sieves. In certain embodiments, the solid surface used in the invention includes, but is not limited to, membrane filter column or magnetic microparticles or spherical beads. The size of the beads is, for example, on the order of diameter of at least 0.2 μm or at least 1 and has a maximum diameter of not more than 10 μm or not more than 6 In certain embodiments, beads of diameter 0.2 μm to 1 μm work well.

The solid support can also carry functional groups which assist in the specific or non-specific binding of nucleic acids, for example, DNA binding proteins, e.g. leucine zippers or histones or intercalating dyes (e.g. ethidium bromide or Hoechst 42945) which can be coated onto the solid support. Likewise, the solid support can also be provided with binding partners to assist in the selective capture of nucleic acids. For example, complementary DNA or RNA sequences, or DNA binding proteins can be used. The attachment of such proteins to the solid phase is achieved using techniques well known in the art. In certain embodiments, the solid surface includes, but is not limited to, silica membrane filter column or silica coated magnetic microparticles/beads, including but not limited to, the SERA-MAG® magnetic particles (see e.g., magnetic particles from Thermo Scientific (Indianapolis, Ind.).

The nucleic acid binding to a solid support is achieved in any way known in the art. Conveniently, the nucleic acid is bound reversibly and non-specifically to the support, i.e., independently of sequence. In certain embodiments, non-specific binding of the desired nucleic acid fragments to the solid phase is achieved by appropriate choice of the solid support and conditions, e.g., the chemical or physical nature of the surface of the solid support, (e.g., hydrophobicity or charge), the pH or composition of the binding buffer. Conveniently, a buffer of appropriate charge and osmolarity is added to the sample prior to, simultaneously with, or after contact with the solid support. Alternative non-specific nucleic acid-support binding techniques use chaotropes for a nucleic acid-binding solid phase such as silica particles, is described, e.g. in EP-A-0389063 (Akzo N.V.). Ionic binding of the nucleic acid to the support may be achieved by using a solid support having a charged surface, for example a support coated with silica and/or polyamines.

The various components are combined and simply allowed to stand for a suitable interval of time to allow the desired nucleic acid fragments to bind to the solid support. Mixing can be performed by any convenient means, including for example simple agitation by stirring or vortexing. Also, if desired, higher or lower temperatures may be used, but are not necessary. The solid support can then be removed from the solution by any convenient means, which depends on the nature of the solid support, and includes all forms of withdrawing the solid support away from the sample supernatant, or vice-versa, including, but not limited to centrifugation, decanting, or pipetting.

The nucleic acid fragments can be precipitated onto the support using any of the known precipitants for nucleic acids, e.g., alcohols, alcohol/salt combinations, and polyethylene glycols (PEGs). Following the nucleic acid binding and/or precipitation steps, one or more washing steps can be introduced. Any conventional washing buffers or other media can be used. Generally speaking, low to moderate ionic strength buffers are preferred, e.g. 20 mM Tris-HCl at pH 8.0/20 mM $C_2H_3NaO_2$. Other standard washing media, e.g. containing alcohols, can also be used, if desired, for example washing with 70% ethanol.

Following the nucleic acid isolation process and any optional washing steps as desired, the support carrying the bound nucleic acid is transferred, e.g., resuspended or immersed into any suitable medium, e.g., water or low ionic strength buffer, for elution and recovery. Elution of the bound nucleic acid fragments with desired size range can readily be achieved using known means, for example by heating to 65° C. for 5 to 10 minutes, following which the support can be removed from the medium, leaving the bound nucleic acid fragments in solution. The invention encompasses any eluting buffer now known or later developed in the art that are suitable to elute and/or release the bound nucleic acids from the solid support to a solution. Exemplary eluting buffer includes, but is not limited to, water and/or any eluting buffer containing low salt, for instance, 10 mM Tris-HCl, pH 8.5.

In certain embodiments, the invention provides a method to selectively recover DNA fragments from a silica membrane filter column with the desired size range by adjusting the chaotrope concentration in the binding buffer. In certain embodiments, the invention provides that only certain DNA, RNA, and/or PNA fragments with a desired size range are able to bind to the silica membrane filter column, and can be subsequently eluted and/or recovered. The desired fragments are less or equal to 100 bp or mers, less or equal to 200 bp or mers, less or equal to 300 bp or mers, less or equal to 400 bp or mers, less or equal to 500 bp or mers, less or equal to 600 bp or mers, less or equal to 700 bp or mers, less or equal to 800 bp or mers, less or equal to 900 bp or mers, or less or equal to 1,000 bp or mers.

In some embodiments, the inventive method comprises mixing the target DNA samples, e.g., 100 μl, with a binding buffer, e.g., 100 μl, comprising 4M guanidium thiocyanate (pH 7.0), wherein each DNA sample mixture, e.g., 200 μl in total, is further diluted with 200 μl, 300 μl, or 400 μl water, before each mixture is separately applied into a silica membrane column. Only DNA fragments less or equal to 100 bp when diluted with 200 μl water with the final concentration of GITC of about 1.0M, DNA fragments less or equal to 200 bp when diluted with 300 μl water with the final concentration of GITC of about 0.8M, and DNA fragments less or equal to 300 bp when diluted with 400 μl water with the final concentration of GITC of about 0.7M, are able to bind to the silica membrane column, and subsequently eluted from the silica membrane filter column and recovered in water and/or an eluting buffer containing low salt.

In other embodiments, the invention provides a method to selectively recover DNA fragments from silica coated microparticles with the desired size range by adjusting the chaotrope concentration in the binding buffer. In certain embodiments, the invention provides that only certain DNA, RNA, and/or PNA fragments with a desired size range are able to bind to the silica coated magnetic beads and can be subsequently eluted and/or recovered. The desired fragments are less or equal to 100 bp or mers, less or equal to 200 bp or mers, less or equal to 300 bp or mers, less or equal to 400 bp or mers, less or equal to 500 bp or mers, less or equal to 600 bp or mers, less or equal to 700 bp or mers, less or equal to 800 bp or mers, less or equal to 900 bp mers, or less or equal to 1,000 bp or mers.

In certain embodiments, the invention method comprises mixing the target DNA samples with a binding buffer comprising 4M guanidium thiocyanate, wherein each DNA sample mixture is further diluted with 200 μl, 300 μl, or 400 μl water, before each mixture is further mixed with silica coated microparticles. Only DNA fragments less or equal to 200 bp when diluted with 200 μl water with the final concentration of GITC of about 1.0M, DNA fragments less or equal to 300 bp when diluted with 300 μl water with the final concentration of GITC of about 0.8M, and DNA fragments less or equal to 400 bp when diluted with 400 μl water with the final concentration of GITC of about 0.7M, are able to bind to the silica coated microparticles, and subsequently eluted from the microparticles and recovered in water and/or an eluting buffer containing low salt.

The invention further provides a method to selectively recover nucleic acid fragments with desired size ranges by adjusting either the salt concentration, or pH, or both, of the first and second binding buffers used in the process. In certain embodiments, the invention provides a method to selectively recover nucleic acid fragments with a desired size range, for instance, 100-1000 bp or mers, 150-950 bp or mers, 150-900 bp or mers, 150-850 bp or mers, 150-800 bp or mers, 150-700 bp or mers, 150-600 bp or mers, 150-500 bp or mers, 150-400 bp or mers, 150-300 bp or mers, 150-200 bp or mers, 200-900 bp or mers, 250-850 bp or mers, 250-700 bp or mers, 300-900 bp or mers, 350-850 bp or mers, 350-700 bp or mers, 400-900 bp or mers, 450-850 bp or mers, 500-900 bp or mers, 500-800 bp or mers, 500-700 bp or mers, 550-950 bp or mers, and any desired size ranges.

In certain embodiments, the first and/or second binding buffer comprises a chaotropic salt including, but not limited to, guanidium hydrochloride (GHCl) in a concentration between 0.8-5.0M, guanidium thiocyanate (GITC) in a concentration between 0.8-5.0M, sodium iodide (NaI) in a concentration between 0.8-7.0M, and sodium perchlorate in a concentration between 1.0-7.0M. In some embodiments, the first binding buffer comprises a low chaotropic salt concentration, for instance, 0.85M guanidine thiocyanate (pH 7.0), whereas the second binding buffer comprises a high chaotropic salt, for instance, 4.0M guanidine thiocyanate (pH 6.5). By adjusting the salt concentrations in the first and second binding buffers, certain nucleic acid fragments are selectively bound to the first or second solid surface, respective, and can be subsequently eluted and recovered from either solid surface in water and/or an eluting buffer.

Figure 5:
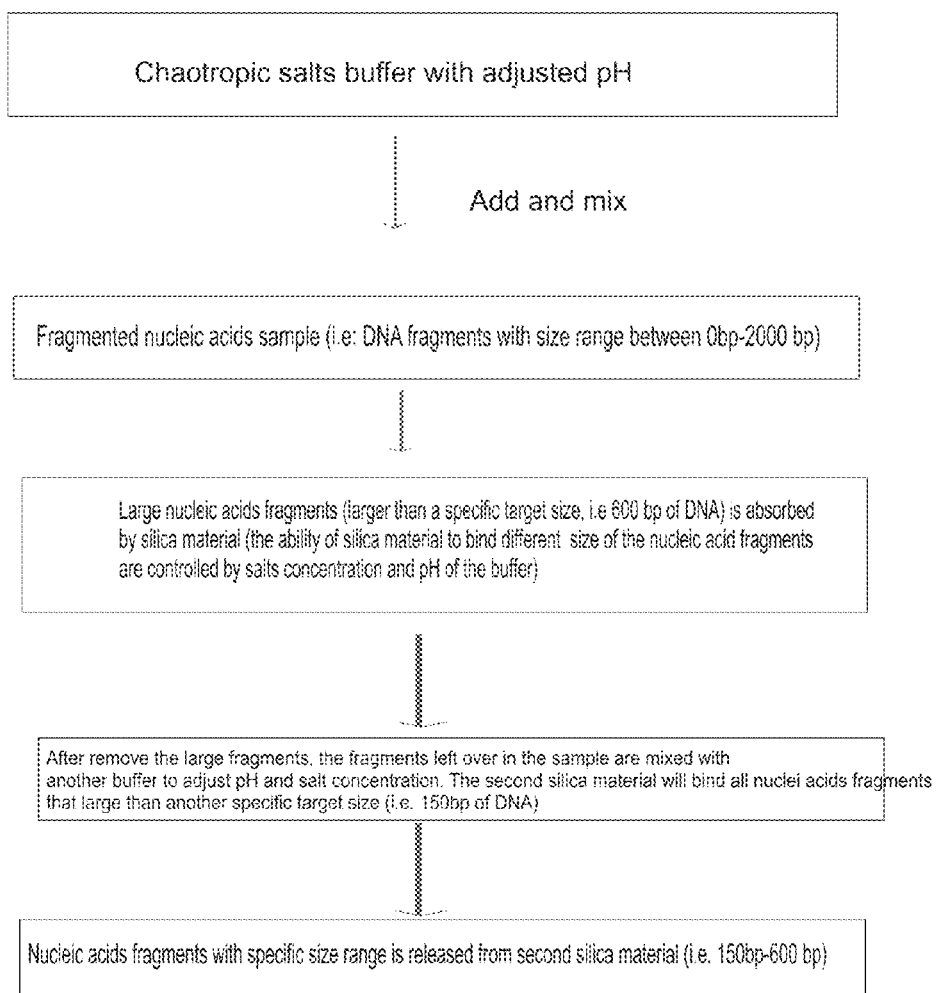
FIG. 5 illustrates nucleic acid size selection workflow.
Figure 6A:
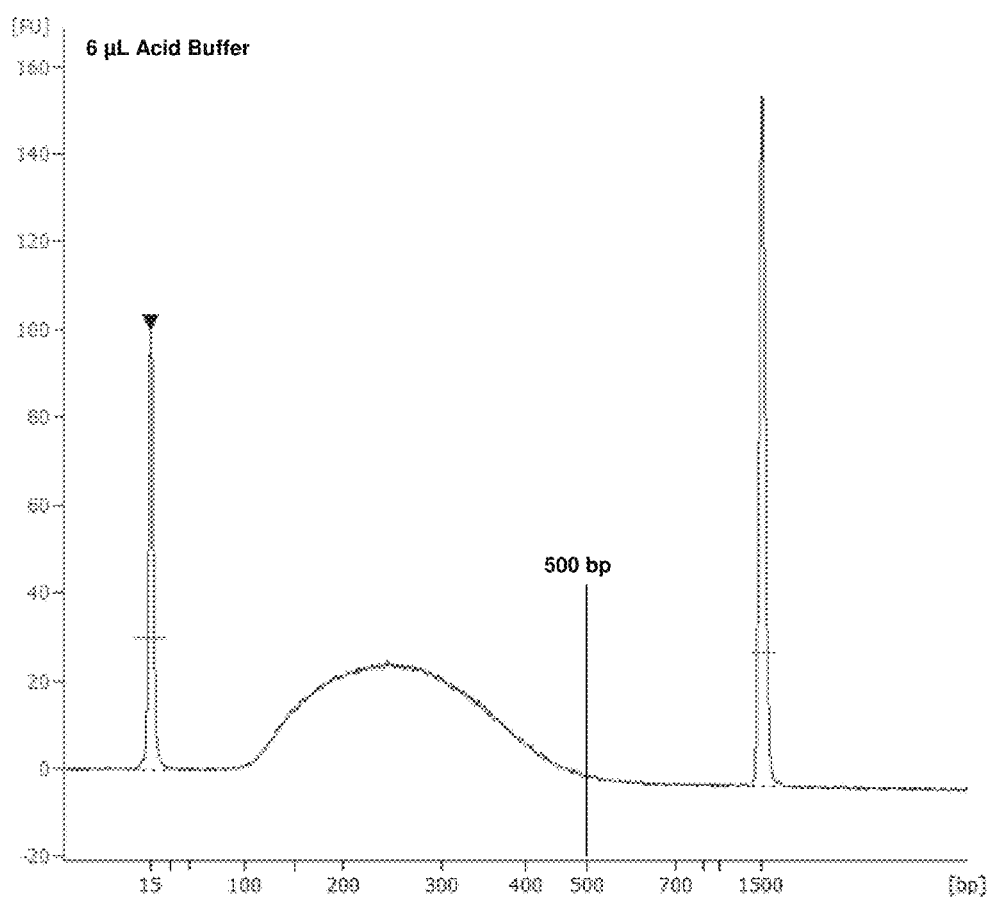
FIGS. 6A-6E illustrate DNA size selection by using different amounts of acidic buffer (e.g., a buffer comprising HCl).
Figure 6B:
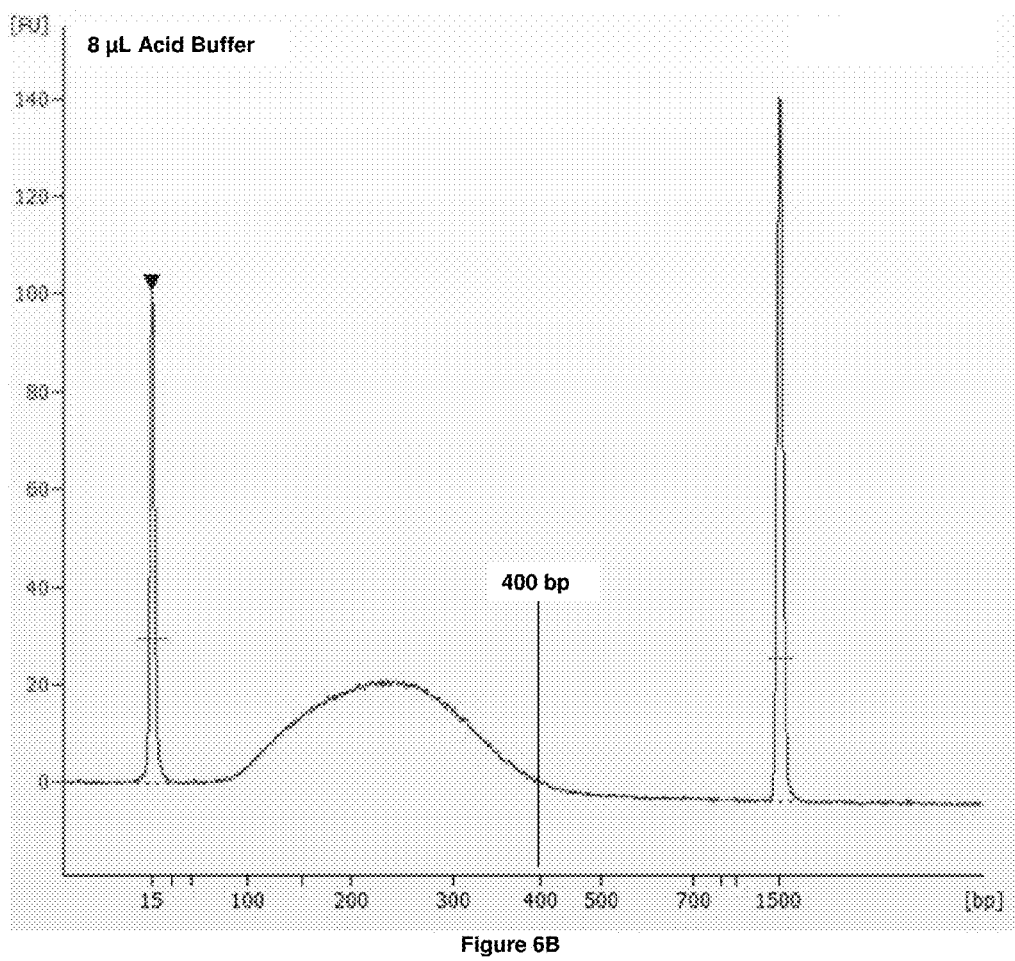
Figure 6C:
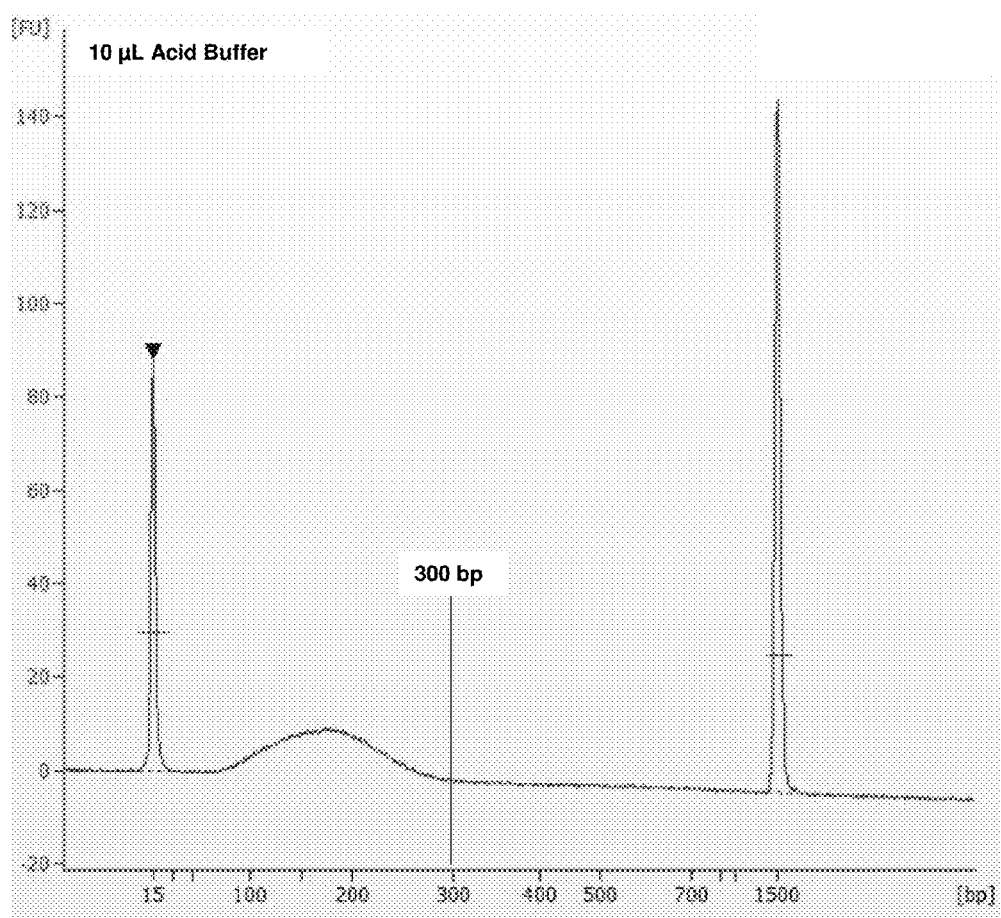
Figure 6D:
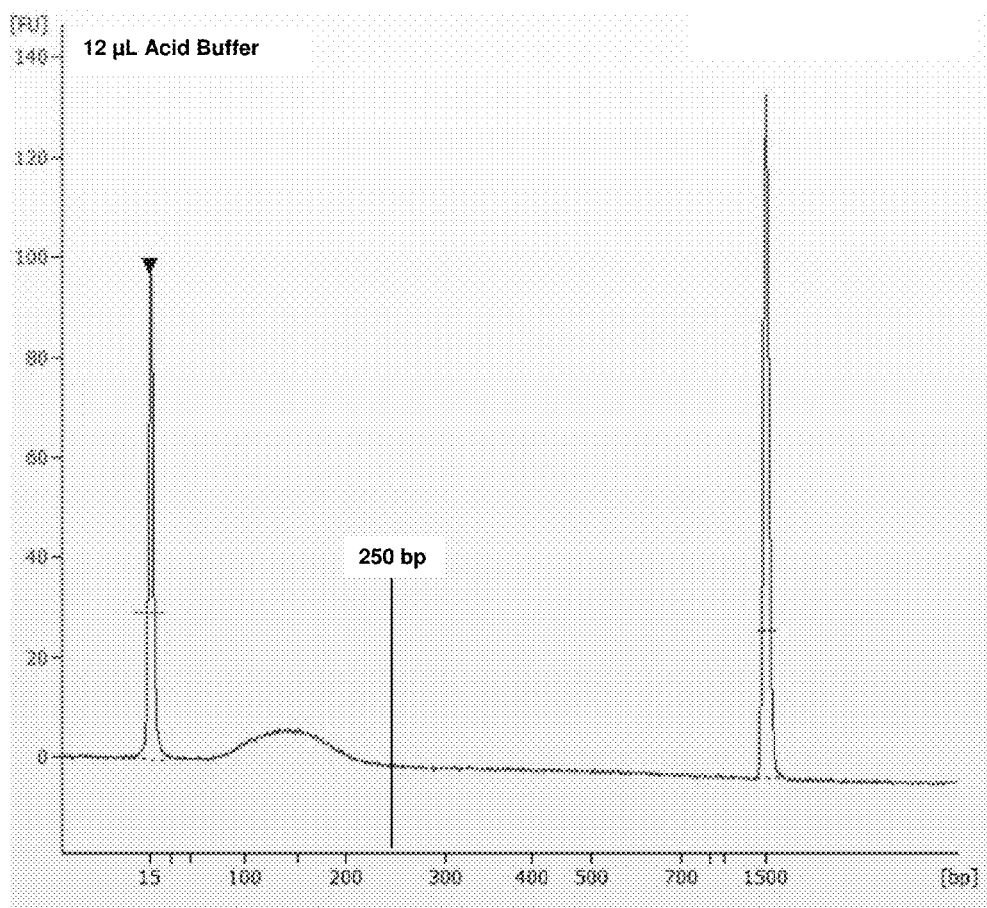
Figure 6E:
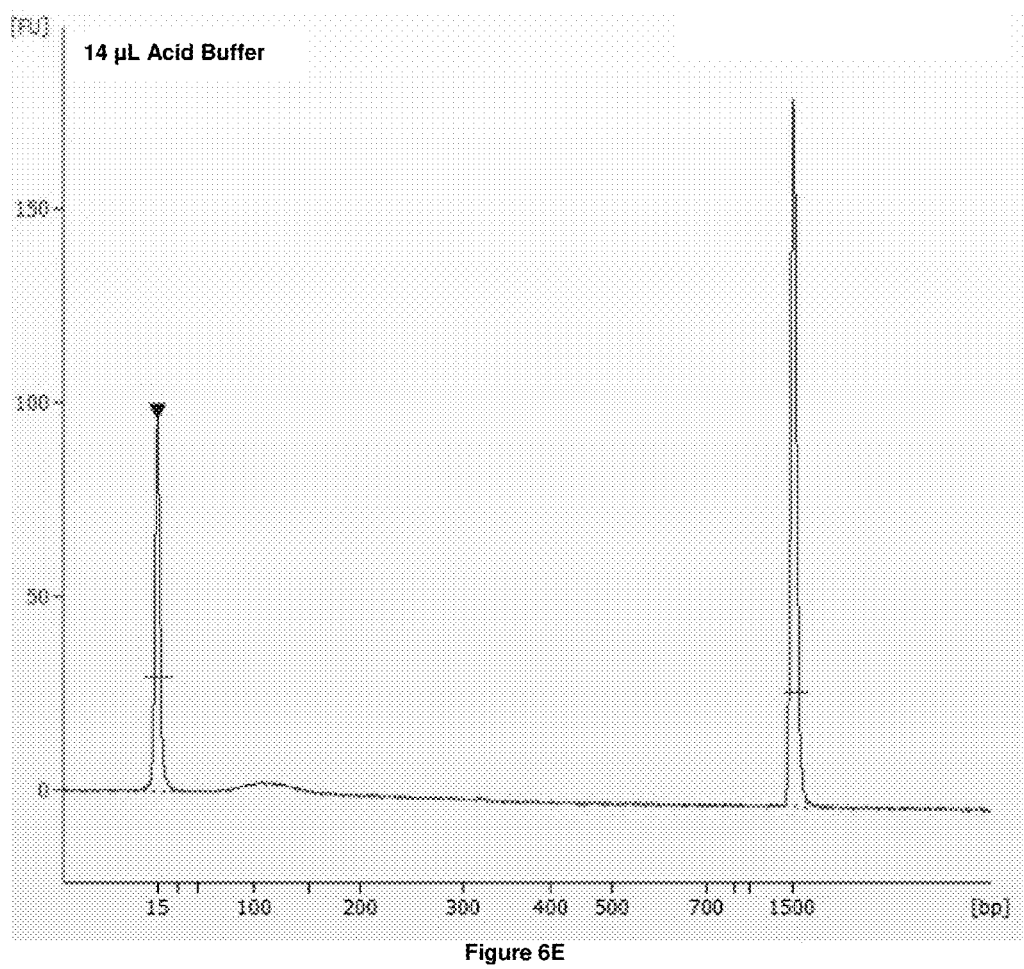
Figure 7A:
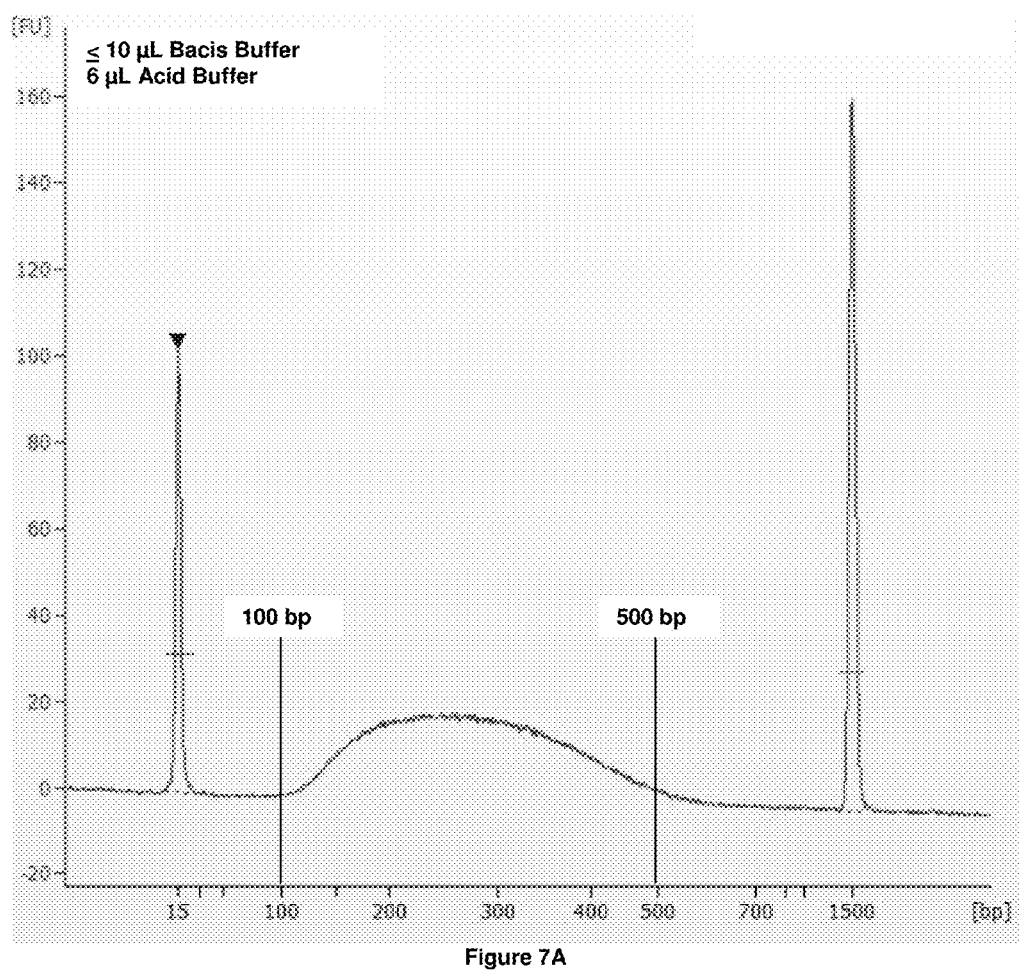
FIGS. 7A-7F illustrate DNA size selection by using different amounts of base buffer (e.g., a buffer comprising NaOH) in conjunction with an acidic buffer.
Figure 7B:
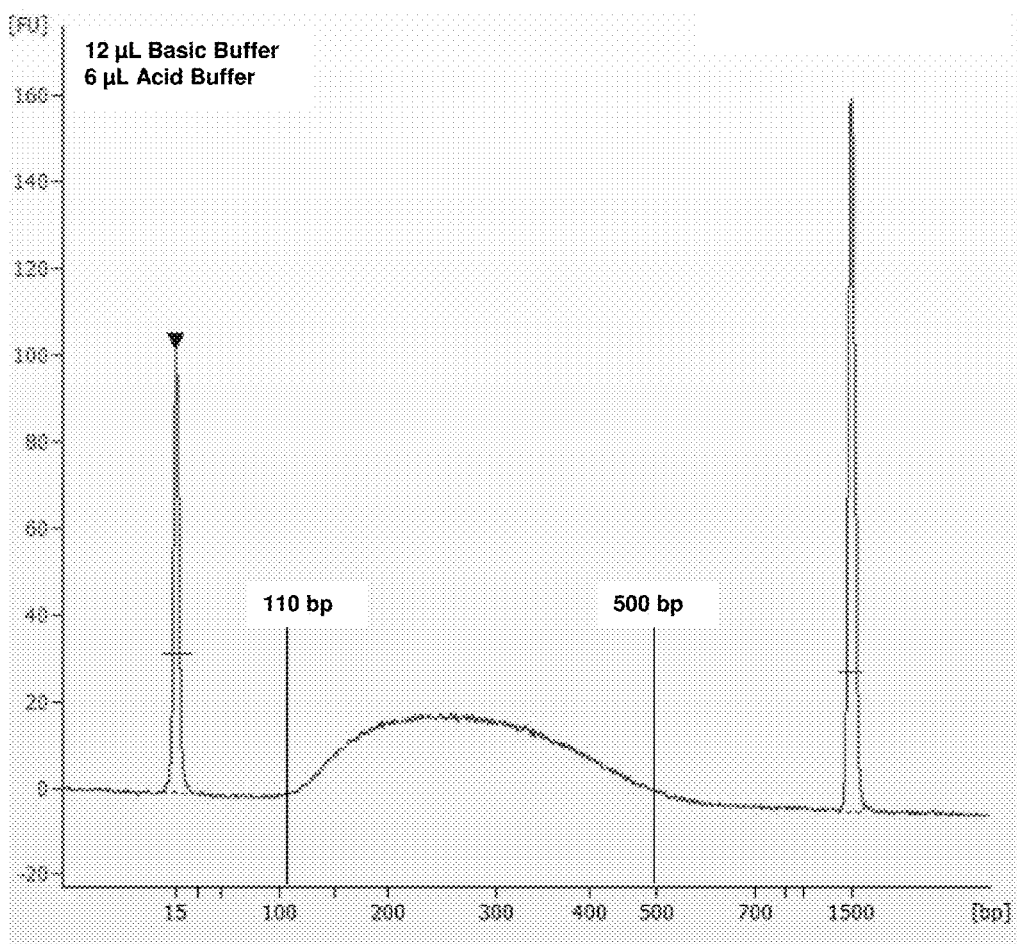
Figure 7C:
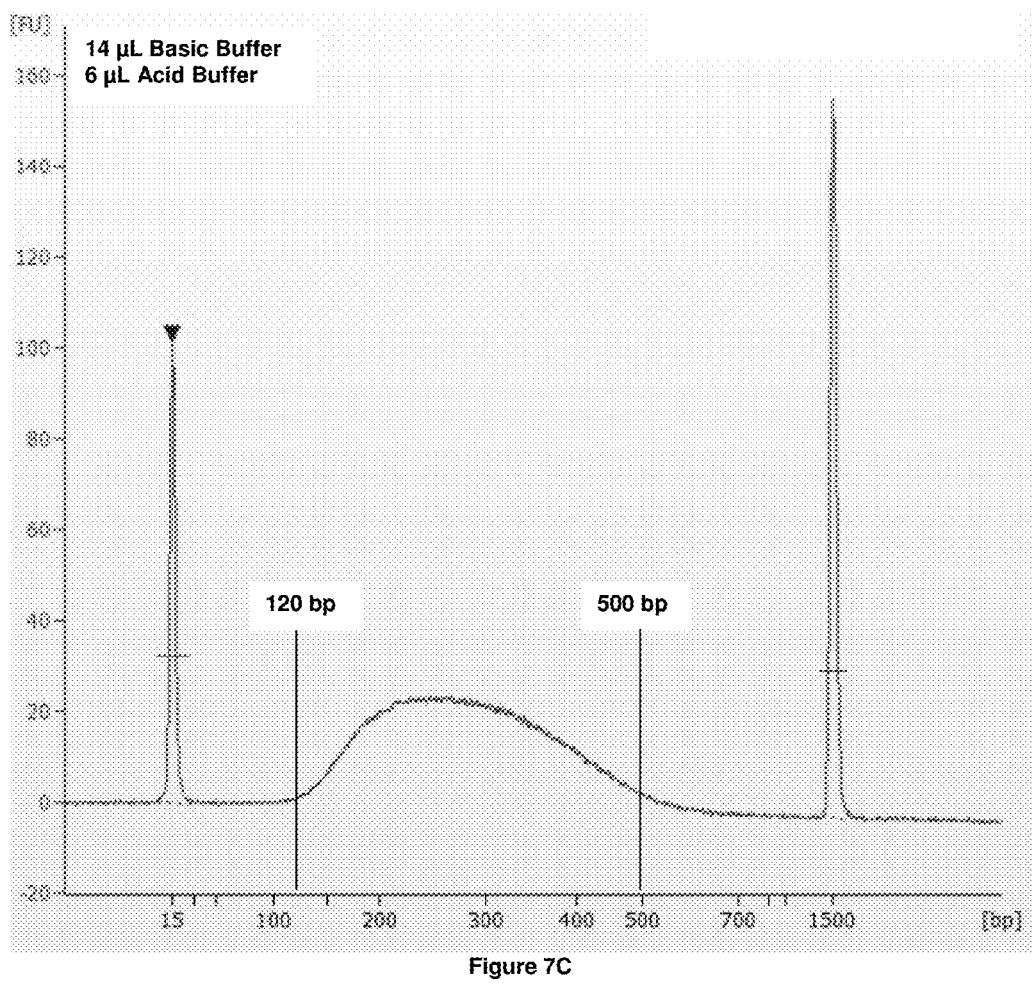
Figure 7D:
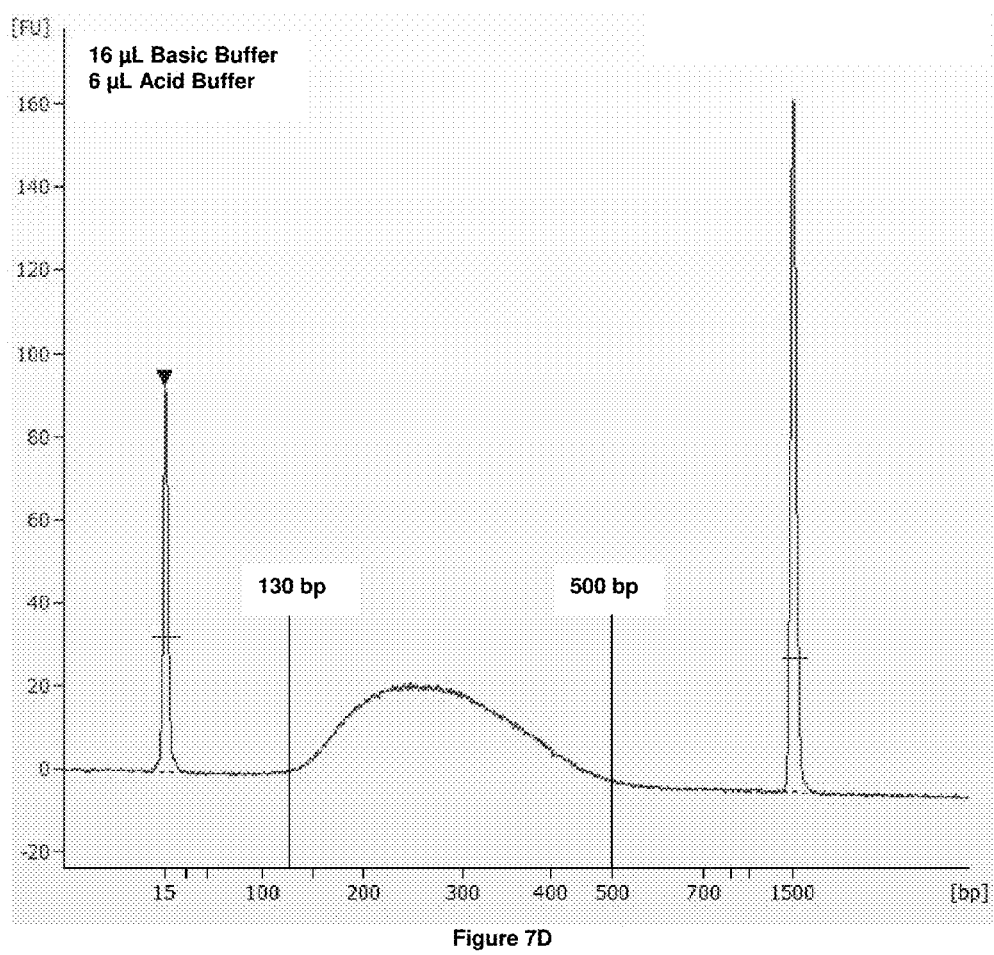
Figure 7E:
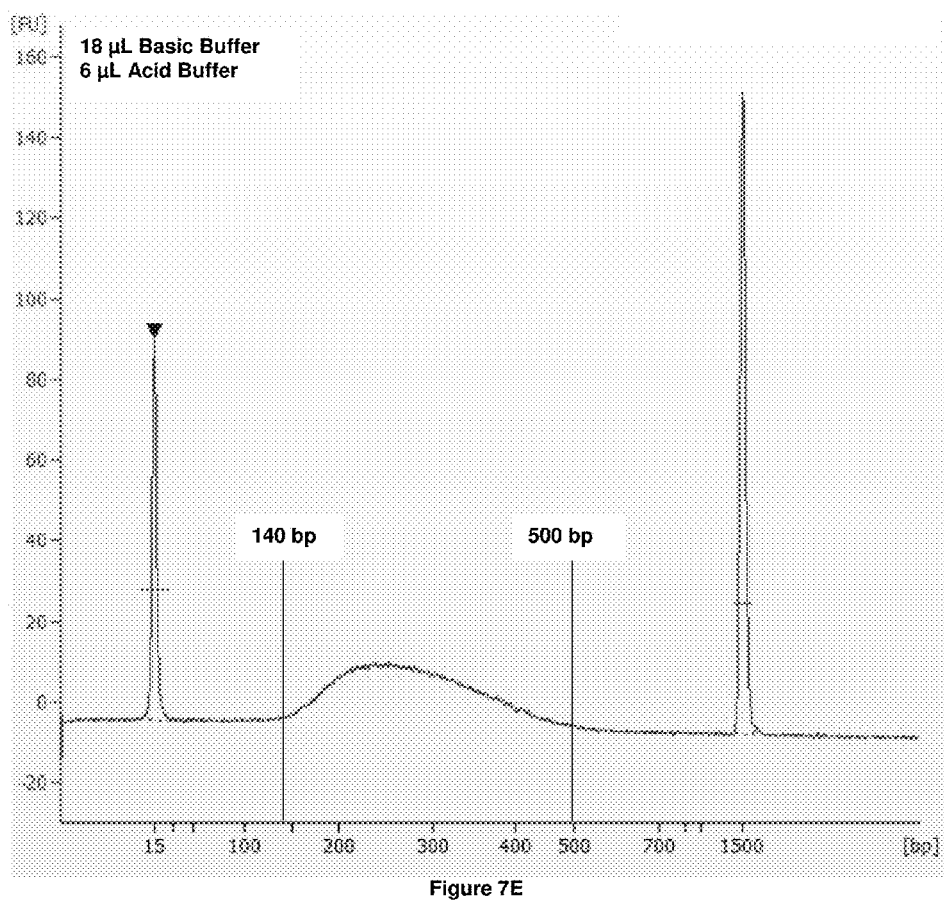
Figure 7F:
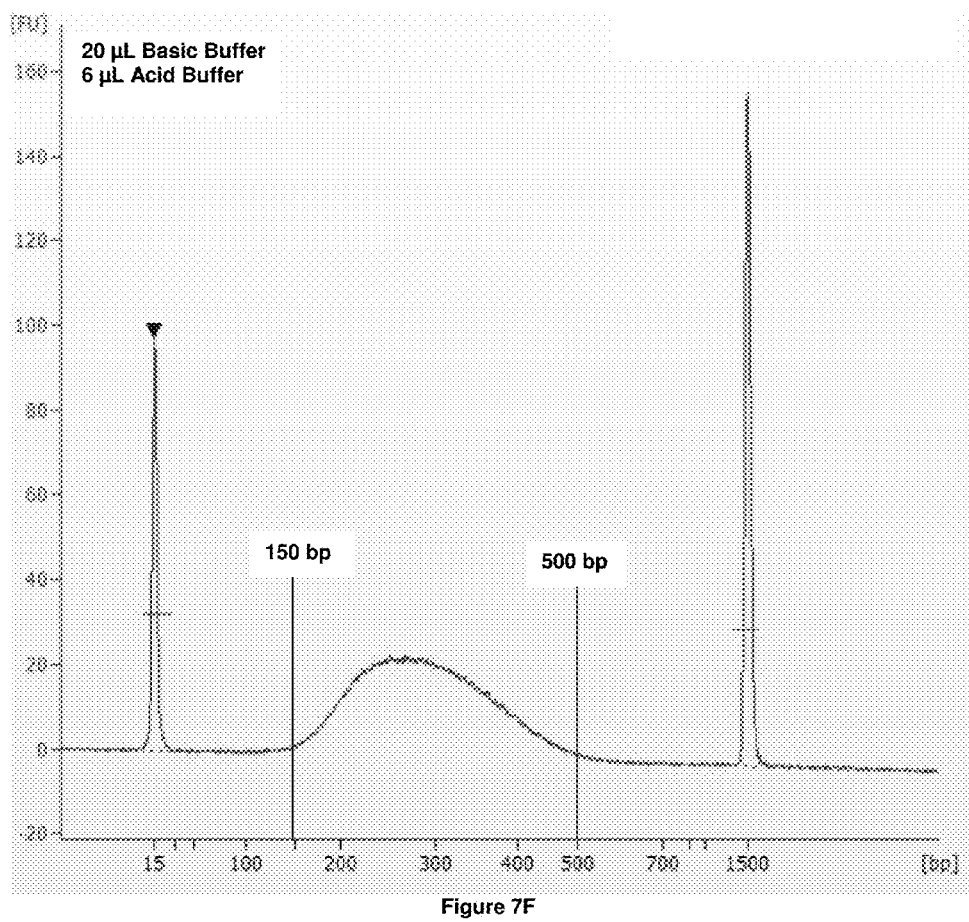

In certain embodiments, the invention method comprises the steps of: a) providing a first sample mixture by mixing target nucleic acids with a first binding buffer, wherein a salt concentration or pH of said first binding buffer is adjusted to allow only larger nucleic acid fragments, e.g., more than 700 bp or mers, more than 600 bp or mers, more than 500 bp or mers, more than 400 bp or mers, and/or more than 300 bp or mers DNA, RNA, or PNA fragments, being able to bind to a solid surface; b) applying said first sample mixture from step a) to the first solid surface; c) collecting a flow-through solution from centrifuging the first solid surface with the first sample mixing; d) providing a second sample mixture by mixing the flow-through solution with a second binding buffer, wherein a salt concentration or pH of said second binding buffer is adjusted to allow nucleic acid fragments with a desired size range, e.g., 150-700 bp or mers, 150-600 bp or mers, 150-500 bp or mers, 150-400 bp or mers, and/or 150-300 bp or mers DNA, RNA, or PNA fragments, being able to bind to a solid surface; e) applying the second sample mixture from step d) to a second solid surface; and e) selectively eluting and recovering the nucleic acid fragments with the desired size range, e.g., 150-700 bp or mers, 150-600 bp or mers, 150-500 bp or mers, 150-400 bp or mers, and/or 150-300 bp or mers DNA, RNA or PNA fragments, by eluting the bound nucleic acid fragments from said second solid surface and recovering them in water and/or an eluting buffer comprising a low salt. FIG. 5 shows the nucleic acids size selection work flow.

In other embodiments, the pH of the first and/or second binding buffer can also be adjusted in order to allow certain nucleic acid fragments with a desired size range to be bound to a solid support. The invention provides that binding ability of nucleic acid fragments is sensitive to pH of the binding buffer. Lower pH facilitates larger nucleic acid fragments' binding ability to a solid surface, whereas smaller nucleic acid fragments lose binding ability to the solid surface when pH increases.

In certain embodiments, as illustrated in the Table above, when the binding buffer contains GITC at a final concentration of about 1.0M, at pH about 5.33, majority of DNA fragments having 500 bp or greater are able to bind to a solid surface; at pH about 4.92, majority of DNA fragments having 400 bp or greater are able to bind to a solid surface; at pH about 3.44, majority of the DNA fragments having 300 bp or greater are able to bind to a solid surface; at pH about 2.57, majority of the DNA fragments having 250 bp or greater are able to bind to a solid surface. In other embodiments, when the binding buffer contains GITC at a final concentration of about 2.5M, at pH about 5.67, majority of DNA fragments having 100 bp or greater are able to bind to a solid surface; at pH about 5.75, majority of DNA fragments having 110 bp or greater are able to bind to a solid surface; at pH about 5.83, majority of the DNA fragments having 120 bp or greater are able to bind to a solid surface; at pH about 5.90, majority of the DNA fragments having 130 bp or greater are able to bind to a solid surface; at pH about 5.96, majority of the DNA fragments having 140 bp or greater are able to bind to a solid surface; and at pH about 6.02, majority of the DNA fragments having 150 bp or greater are able to bind to a solid surface. As used herein, the term "majority" means more than 50%, more than 55%, more than 60%, more than 65%, more than 70%, more than 75%, more than 80%, more than 85%, more than 90%, and more than 95% of the total DNA, RNA, and/or PNA fragments in a purification nucleic acid sample.

Methods for adjusting pH of a binding buffer are well known in the art. In certain embodiments, the pH of a binding buffer is adjusted using an acid or acidic salt, such as Tris-HCl, sodium phosphate, or other phosphate salt, to allow larger nucleic acid fragments to be bound to the solid surface. For instance, an acidic buffer comprising HCl can be mixed with a binding buffer comprising GITC and Tris-HCl to decrease the pH of the binding buffer so as to adjust the binding ability of different size nucleic acid fragments. In other embodiments, the pH of a binding buffer is adjusted using a base or basic salt, such as NaOH, to remove smaller nucleic acid fragments and allow only certain nucleic acid fragments with desired size ranges to be bound to the solid surface, and subsequently recovered therefrom. For instance, a basic buffer comprising NaOH can be mixed with a binding buffer comprising GITC and Tris-HCl to increase pH of the binding buffer so as to adjust the binding ability of different size nucleic acid fragments. The nucleic acid fragment size selections corresponding to the volumes of the acid and/or basic buffer used in adjusting the pH of the binding buffer are illustrated in FIGS. 6 and 7. In certain embodiments, the pH of the binding buffer ranges between 5.5 and 7.5. The scope of the invention is not limited to the materials and/or methods to be used for adjusting the pH of the binding buffer.

Kits for selectively recovering nucleic acid fragments with desired size ranges are also provided by the invention. The inventive kits comprise: a) one or more binding buffers for selective binding of nucleic acid fragments to a solid phase; b) a solid phase coated with a functional group on the surface; c) other reagents for nucleic acid purification and recovery; and d) instructions providing protocols for selective recovery of nucleic acid fragments with desired size ranges. In certain embodiments, the solid phase is silica membrane filter column or silica coated magnetic microparticles. In certain embodiments, the reagents for nucleic acid purification and recovery process include, but not limited to, wash buffer, eluting buffer, and/or water, as discussed above.

Therefore, the inventive size selection method and/or kit provide a convenient system for selective recovery of nucleic acid fragments free of oligonucleotides, nucleotides, and polymerase with recovery rate exceeding 50%, thus, providing a fast and reliable recovery of nucleic acid fragments from various enzymatic reaction steps in the next generation steps (NGS) in the library construction, as well as with library construction workflows for all the common NGS platforms such as Illumina HiSeq/GA/MiSeq, Roche 454 Genome Sequencer and Life Technologies SOLiD. In certain embodiments, the inventive size selection methods and/or kits provide a selection of the cut-off size between 100-300 bp or mers and/or 150-300 bp or mers. In other embodiments, the inventive size selection methods and/or kits provide selective recovery of nucleic acid fragments between 150-700 bp or mers by adjusting the nucleic acid binding condition with appropriate volumes of the specifically formulated binding buffers with the adjusted chaotropic salt concentration and pH of the buffer before loading to a solid phase column and/or bead.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to certain embodiments of the invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

Other features and advantages of the invention will be apparent from the following description of certain embodiments thereof and from the claims. These and many other variations and embodiments of the invention will be apparent to one of skill in the art upon a review of the appended description and examples.

EXAMPLES

Example 1

DNA Fragment Selection and Recovery from Silica Membrane Filter Column 0.1 ml 100 bp DNA ladder (Omega Bio-tek, Inc., Norcross, Ga.) was mixed with 100 μl of a DNA size selection binding buffer comprising guanidine thiocyanate (4M), Tri-HCl (100 mM, pH 7.0), and EDTA (10 mM) in a microcentrifuge tube. The DNA sample mixture was inverted 10 times, incubated at room temperature for 5 minutes, diluted with water by adding 200 μl, 300 μl, and 400 μl water, respectively, and then further mixed by inverting each tube for 10 times. Each mixed solution was subsequently transferred to a silica fabric filter column (Omega Bio-Tek, Inc., Norcross, Ga.) and centrifuged at 13,000×G for 1 minute for DNA binding to the column. The column with DNA bound thereon was washed with 70% ethanol twice by centrifugation at 13,000×G for 1 minute each, and was dried by centrifuged at 13,000×G for 3 minutes. After wash and dry, fifty (50) μl eluting buffer comprising Tris-HCl (10 mM pH 8.5) was then added into the column, followed-up by a centrifugation of the column for 5 minutes to elute the bound DNA fragments from the column.

FIG. 1 shows the results on EtBr-stained agarose gel electrophoresis illustrating the separation and selection of DNA fragments eluted and recovered from the silica membrane filter column using DNA size selection binding buffer diluted with different amount of water. The results indicate that 1) diluting the DNA sample mixture with 200 μl water, the DNA fragments with a size less or equal to 100 bp were completely eluted and/or recovered from the silica membrane column; 2) diluting the DNA sample mixture with 300 μl water, the DNA fragments with a size less or equal to 200 bp were completely eluted and/or recovered from the silica membrane column; and 3) diluting the DNA sample mixture with 400 μl water, the DNA fragments with a size less or equal to 300 bp were completely eluted and/or recovered from the silica membrane column.

Example 2

DNA Fragment Selection and Recovery from Silica Coated Paramagnetic Particles/Beads 0.1 ml 100 bp DNA ladder (Omega Bio-Tek, Inc., Norcross, Ga.] was mixed with 100 μl of DNA size selection binding buffer comprising guanidine thiocyanate (4M), Tri-HCl, (100 mM, pH 7.0), and EDTA (10 mM) in a microcentrifuge tube. The DNA sample mixture was inverted 10 times, incubated at room temperature for 5 minutes, diluted with water by adding 0 µl, 100 µl, 200 µl, 300 µl, 400 µl, 500 µl, and 600 µl water, respectively, and then further mixed by inverting each tube for 10 times. Each mixed solution was further mixed with silica coated magnetic particles/beads (Omega Bio-Tek, Atlanta, Ga.) by adding 10 particles/beads at 50 mg/ml and inverting the mixed solution for 10 times. The magnetic particles/beads were collected by placing the tube to a magnetic stand (Omega Bio-Tek, Inc., Norcross, Ga.) for 2 minutes. After completely aspirate and discard the cleared supernatant liquid from each tube using a pipette, 500 µl of 70% ethanol was added to each tube and mixed by vortexing for 1 minute to suspend the magnetic particles/beads. Each tube was then placed on the magnetic stand for another 1 minute to collect the magnetic particles/beads, followed-up complete aspiration and discarding the cleared supernatant liquid from each tube using a pipette. Each tube was further left on the magnetic stand for additional 5 minutes to let the magnetic particles/beads dry. Fifty (50) µl eluting buffer comprising Tris-HCl (10 mM, pH 8.5) was then added to each tube and the magnetic particles/beads were resuspended by vortexing for 30 seconds to elute DNA.

Figure 2:
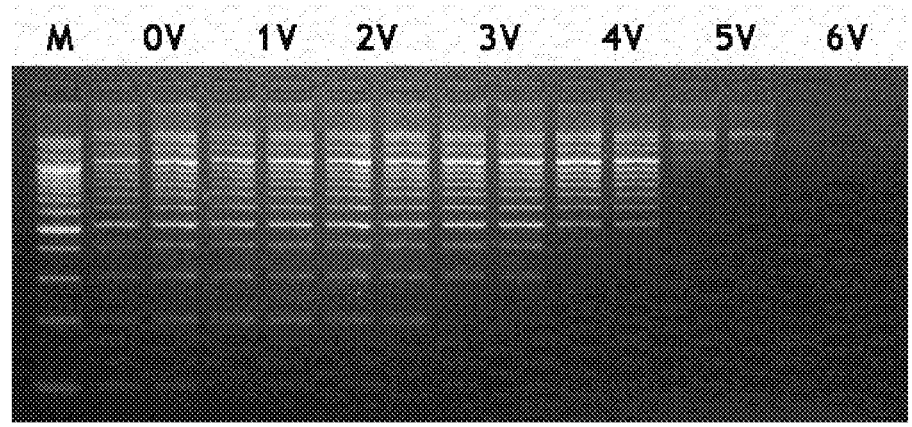
FIG. 2 shows the results on EtBr-stained agarose gel electrophoresis illustrating the separation and selection of DNA fragments eluted and recovered from silica magnetic particles/beads using a DNA size selection binding buffer diluted with different amounts of water.

FIG. 2 shows the results on EtBr-stained agarose gel electrophoresis illustrating the separation and selection of DNA fragments eluted and recovered from silica magnetic particles/beads using the DNA size selection binding buffer diluted with different amount of water. The results indicate that: 1) diluting the DNA sample mixture with 200 µl water, the DNA fragments with a size less or equal to 200 bp were completely eluted and/or recovered from the silica magnetic particles/beads; 2) diluting the DNA sample mixture with 300 µl water, the DNA fragments with a size less or equal to 300 bp were completely eluted and/or recovered from the silica magnetic particles/beads; and 3) diluting the DNA sample mixture with 400 µl water, the DNA fragments with a size less or equal to 400 bp were completely eluted and/or recovered from the silica magnetic particles/beads.

Example 3

Effects of Salt Concentrations in DNA Size Binding Buffers on DNA Fragment Selection and Recovery 0.1 ml 100 bp DNA ladder (Omega Bio-Tek, Inc., Norcross, Ga.) was mixed with 350 µl, 400 µl and 500 µl first binding buffer comprising guanidine thiocyanate (0.85M), Tri-HCl (100 mM, pH7.0), and EDTA (10 mM) in a microcentrifuge tube. This first DNA sample mixture was inverted 10 times and incubated at room temperature for 5 minutes. Each mixed solution was then transferred to a first silica fabric filter column (Omega Bio-Tek, Inc., Norcross, Ga.) and centrifuged at 13,000×G for 1 minute for larger DNA to be bound to the column. The flow-through liquid was collected and then mixed with 30 µl second binding buffer comprising guanidine thiocyanate (4M) and Tri-HCl (100 mM, pH6.5). This second DNA mixture solution was then loaded into a second silica fabric filter column and centrifuged at 13,000×G for 1 minute. Every first and second columns were then washed with 70% ethanol twice by centrifugation at 13,000×G for 1 minute, followed-up further centrifugation at 13,000×G for 3 minutes to dry the columns. Forty (40) µl elution buffer comprising 10 mM Tris-HCl, (pH 8.5) was then added into each column and followed-up centrifugation for 5 minutes to elute DNAs from the columns.

Figure 3:
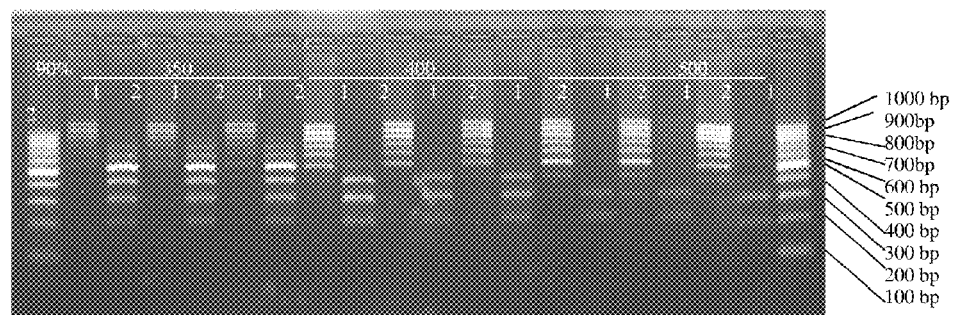
FIG. 3 shows the results on EtBr-stained agarose gel electrophoresis illustrating the separation and selection of DNA fragments in different size range by adjusting the salt concentrations in DNA size selection binding solutions and eluting the targeted DNA fragments from the first and second silica columns with low salt buffer and/or water.

FIG. 3 shows the results on EtBr-stained agarose gel electrophoresis illustrating the separation and selection of DNA fragments in different size range by adjusting the salt concentrations in DNA size selection binding solutions and eluting the targeted DNA fragments from the first and second silica columns with low salt buffer and/or water. The results shows: 1) when adding 350 µl first binding buffer comprising guanidine thiocyanate (0.85M), Tri-HCl (100 mM, pH7.0), and EDTA (10 mM) into the DNA mixture sample, the DNA fragments with the size larger than 700 bp were able to bind onto the first silica fabric filter column, and when subsequently adding 30 µl second binding buffer comprising guanidine thiocyanate (4M) and Tri-HCl (100 mM, pH6.5) into the flow-through liquid collected from the first silica column, the DNA fragments with the size between 200 bp to 700 bp were eluted and/or recovered from the second silica column; 2) when adding 400 µl binding buffer comprising guanidine thiocyanate (0.85M), Tri-HCl (100 mM, pH7.0), and EDTA (10 mM) into the DNA mixture sample, the DNA fragments with the size larger than 500 bp were able to bind onto the first silica column, and when subsequently adding 30 µl second binding buffer comprising guanidine thiocyanate (4M) and Tri-HCl (100 mM, pH6.5) into the flow-through liquid collected from the first silica column, the DNA fragments with the size between 200 bp to 500 bp were eluted and/or recovered from the second silica column; and 3) when adding 500 µl binding buffer comprising guanidine thiocyanate (0.85M), Tri-HCl (100 mM, pH7.0), and EDTA (10 mM) into the DNA mixture sample, the DNA fragments with the size larger than 300 bp were able to bind onto the first silica column, and when subsequently adding 30 µl second binding buffer comprising guanidine thiocyanate (4M) and Tri-HCl (100 mM, pH6.5) into the flow-through liquid collected from the first silica column, the DNA fragments with the size between 200 bp to 300 bp were eluted and recovered from the second silica column.

Example 4

Effects of pH in DNA Size Binding Buffers on DNA Fragment Selection and Recovery Each microcentrifuge tube contains a mixture of 0.1 ml 100 bp DNA ladder (Omega Bio-Tek, Inc., Norcross, Ga.) and 400 µl first binding buffer comprising guanidine thiocyanate (1.3M) and sodium dihydrogen phosphate (0.3M) at about pH 5.8, pH 5.9, pH 6.0, pH 6.1, and pH 6.2. Each tube with the DNA mixture sample was inverted 10 times and incubated at room temperature for 5 minutes. The DNA sample mixture solution from each tube was them transferred to a first silica fabric filter column (Omega Bio-Tek, Atlanta, Ga.) and centrifuged at 13,000×G for 1 minute, separately, for larger DNA to be bound to the column. The flow-through liquid from the first silica column were collected and mixed with 100 µl second binding buffer comprising guanidine thiocyanate (4M) and Tri-HCl (100 mM, pH6.5). Each mixture with the second binding buffer was then loaded into a second silica fabric filter column and centrifuged at 13,000×G for 1 minute. Every first and second columns were then washed with 70% ethanol twice by centrifugation at 13,000×G for 1 minute, followed-up by further centrifugation at 13,000×G for 3 minutes to dry the columns. Forty (40) µl elution buffer comprising 10 mM Tris-HCl, (pH 8.5) was then added into each column and followed-up by centrifugation for 5 minutes to elute DNAs from the columns.

Figure 4:
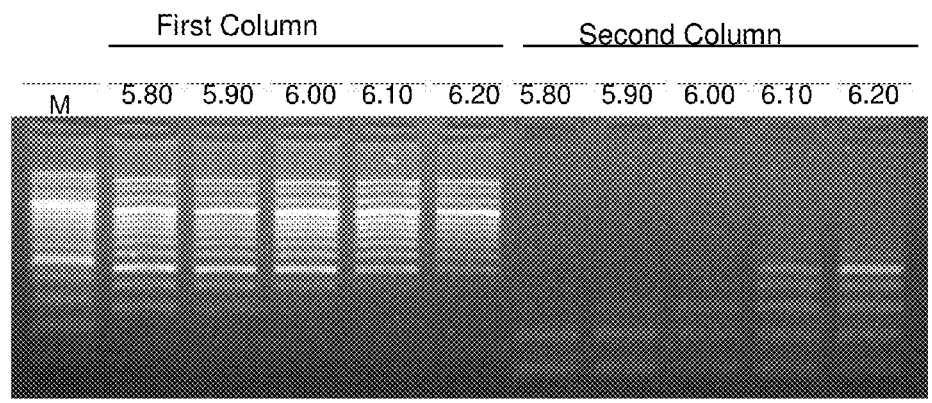
FIG. 4 shows the results on EtBr-stained agarose gel electrophoresis illustrating that pH conditions in DNA size selection binding buffers affect the separation and selection of different size DNA fragments eluted and recovered from a silica column with low salt elution buffer.

FIG. 4 shows the results on EtBr-stained agarose gel electrophoresis illustrating that pH conditions in DNA size selection binding buffers affect the separation and selection of different size DNA fragments eluted and recovered from a silica column with low salt elution buffer. The results demonstrate that the binding ability of DNA fragments to the silica membrane column is very sensitive to the pH of the binding buffer. The smaller DNA fragments are, the less binding ability, when pH increased.

While the invention has been described in some detail for purpose of clarity and understanding, it will be appreciated by one skilled in the art from a reading of this disclosure that various changes in form and detail can be made without departing from the true scope of the invention and appended claims.

What is claimed:

1. A method to selectively recover nucleic acid fragments with a desired size range comprising:
    a) mixing target nucleic acids with a binding buffer having a selected pH and chaotropic salt concentration to allow the nucleic acid fragments with the desired size range to be bound to a solid surface, wherein said chaotropic salt comprises guanidinium thiocyanate (GITC) in a final concentration between 0.7-1M;
    b) applying the mixture from step a) to the solid surface so that the nucleic acid fragments with the desired size range reversibly and non-specifically bind to the solid surface; and
    c) selectively recovering the nucleic acid fragments with the desired size range by eluting the bound nucleic acid fragments from the solid surface with an eluting buffer.

2. The method of claim 1, wherein said chaotropic salt concentration of said binding buffer is adjusted by water in an amount that allows said nucleic acid fragments with the desired size range being bound to and subsequently eluted from said solid surface.

3. The method of claim 2, wherein said solid surface is silica membrane filter column or silica coated magnetic microparticles.

4. The method of claim 3, wherein said nucleic acid fragments are DNA fragments, RNA fragments, or PNA fragments.

5. The method of claim 4, wherein DNA fragments with the desired size range less or equal to 100 bp bind to and subsequently eluted from a silica membrane filter column, when the final concentration of GITC in the binding buffer is about 1.0M.

6. The method of claim 4, wherein DNA fragments with the desired size range less or equal to 200 bp bind to and subsequently eluted from a silica membrane filter column when the final concentration of GITC in the binding buffer is about 0.8M.

7. The method of claim 4, wherein DNA fragments with the desired size range less or equal to 300 bp bind to and subsequently eluted from a silica membrane filter column when the final concentration of GITC is about 0.7M.

8. A method to selectively recover nucleic acid fragments with a desired size range comprising:
    a) providing a first sample mixture by mixing target nucleic acids with a first binding buffer, wherein a chaotropic salt concentration or pH of said first binding buffer is adjusted to allow nucleic acid fragments of more than 700 bps to bind to a solid surface;
    b) applying said first sample mixture from step a) to a first solid surface;
    c) collecting a flow-through solution from centrifuging the first solid surface with the first sample mixture;
    d) providing a second sample mixture by mixing the flow-through solution with a second binding buffer, wherein a chaotropic salt concentration or pH of said second binding buffer is adjusted to allow nucleic acid fragments with a desired size range of 100 to 700 bps to bind to a solid surface, wherein said chaotropic salt comprises guanidinium thiocyanate (GITC) in a final concentration between 0.7-1M;
    e) applying the second sample mixture from step d) to a second solid surface; and
    f) selectively recovering the nucleic acid fragments with the desired size range of 100 to 700 bps by separately eluting the bound nucleic acid fragments from the second solid surfaces with an eluting buffer.

9. The method of claim 8, wherein said first binding buffer comprises an acid or an acidic salt thereof, to reduce pH of the binding buffer so as to facilitate larger nucleic acid fragments to be bound to the solid surface.

10. The method of claim 8, wherein said second binding buffer comprises a base, or basic salt thereof, to increase pH of the binding buffer so as to remove smaller nucleic acid fragments.

11. The method of claim 8, wherein pH of said binding buffers ranges between 5.5 and 7.5.

* * * * *